(12) United States Patent
Knight et al.

(10) Patent No.: US 12,420,142 B2
(45) Date of Patent: *Sep. 23, 2025

(54) SYSTEM AND METHOD FOR DETECTING FATIGUE AND PROVIDING COACHING IN RESPONSE

(71) Applicant: Under Armour, Inc., Baltimore, MD (US)

(72) Inventors: Jeff Knight, Austin, TX (US); F. Grant Kovach, Baltimore, MD (US); Paul Winsper, Portland, OR (US); Michael Mazzoleni, Baltimore, MD (US); Jeffrey Allen, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 529 days.

This patent is subject to a terminal disclaimer.

(21) Appl. No.: 17/738,793

(22) Filed: May 6, 2022

(65) Prior Publication Data

US 2022/0387852 A1 Dec. 8, 2022

Related U.S. Application Data

(63) Continuation of application No. 16/589,720, filed on Oct. 1, 2019, now Pat. No. 11,325,002.

(51) Int. Cl.
*A63B 24/00* (2006.01)
*A61B 5/00* (2006.01)
(Continued)

(52) U.S. Cl.
CPC ........ *A63B 24/0062* (2013.01); *A61B 5/0002* (2013.01); *A61B 5/1038* (2013.01);
(Continued)

(58) Field of Classification Search
CPC .......... A63B 24/0062; A63B 2220/836; A63B 24/0075; A61B 5/1038; A61B 5/1112;
(Continued)

(56) References Cited

U.S. PATENT DOCUMENTS 6,898,550 B1 5/2005 Blackadar
9,247,897 B2 2/2016 Darley et al.
(Continued)

*Primary Examiner* — Devin B Henson
(74) *Attorney, Agent, or Firm* — Maginot, Moore & Beck, LLP

(57) ABSTRACT

A method of operating a fitness tracking system includes receiving at least one first value and at least one second value for at least one foot action parameter from a sensor during a user workout. The method further includes determining whether the user has experienced a first type of fatigue and a second type of fatigue based on the at least one first value and the at least one second value, wherein the first type of fatigue is defined by different rules than the second type of fatigue. When it is determined that the user experienced the first type of fatigue, a first recommended action is provided to the user via a personal electronic device of the user. When it is determined that the user experienced the second type of fatigue, a second recommended action is provided to the user via the personal electronic device.

13 Claims, 10 Drawing Sheets

(51) Int. Cl.
  *A61B 5/103*    (2006.01)
  *A61B 5/11*     (2006.01)

(52) U.S. Cl.
  CPC ............ *A61B 5/486* (2013.01); *A61B 5/6807* (2013.01); *A61B 5/7282* (2013.01); *A61B 5/7405* (2013.01); *A61B 5/7435* (2013.01); *A61B 5/7455* (2013.01); *A61B 5/7475* (2013.01); *A63B 24/0075* (2013.01); *A61B 5/1112* (2013.01); *A63B 2220/836* (2013.01)

(58) Field of Classification Search
  CPC ... A61B 5/6807; G16H 20/30; G09B 19/0038
  See application file for complete search history.

(56) References Cited

U.S. PATENT DOCUMENTS

| | | | |
|---|---|---|---|
| 9,694,239 B2 * | 7/2017 | Case, Jr. ............ | A63B 24/0003 |
| 11,325,002 B2 * | 5/2022 | Knight ................ | A61B 5/7435 |
| 2008/0198378 A1 | 8/2008 | Kuratsune et al. | |
| 2008/0258921 A1 | 10/2008 | Woo et al. | |
| 2013/0106603 A1 | 5/2013 | Weast et al. | |
| 2014/0222173 A1 | 8/2014 | Gledwoyn | |
| 2016/0151228 A1 | 6/2016 | Fujikake | |
| 2016/0324445 A1 * | 11/2016 | Kim .................... | A61B 5/6802 |
| 2016/0345865 A1 | 12/2016 | Agrawal et al. | |
| 2017/0188894 A1 | 7/2017 | Chang et al. | |
| 2017/0273615 A1 | 9/2017 | Oleson et al. | |

* cited by examiner

| | $t_0$ | $t_1$ | $t_2$ | $t_3$ | $t_4$ | $t_5$ | $t_6$ | $t_7$ | $t_8$ | $t_9$ | $t_{10}$ | $t_{11}$ |
|---|---|---|---|---|---|---|---|---|---|---|---|---|
| Speed | 6.5 | 6.2 | 6.5 | 6.1 | 6.5 | 6.0 | 6.0 | 6.1 | 5.8 | 5.8 | 5.9 | 6.0 |
| Cadence | 180 | 190 | 180 | 178 | 172 | 175 | 180 | 178 | 140 | 140 | 141 | 142 |
| GCT | 300 | 310 | 290 | 320 | 300 | 320 | 340 | 310 | 400 | 390 | 400 | 400 |
| FSA | 2 | 2 | 2 | 3 | 3 | 3 | 4 | 2 | 15 | 18 | 18 | 19 |

SYSTEM AND METHOD FOR DETECTING FATIGUE AND PROVIDING COACHING IN RESPONSE

CROSS-REFERENCE TO RELATED APPLICATIONS

This patent application is a continuation of U.S. patent application Ser. No. 16/589,720, filed Oct. 1, 2019, now U.S. Pat. No. 11,325,002, issued May 10, 2022.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent flies or records, but otherwise reserves ail copyright rights whatsoever.

FIELD

The present invention generally relates to devices and methods for monitoring athletes during workout sessions and other athletic events.

BACKGROUND

A recent trend in fitness is using a wearable device to record data related to the activity a user is performing. The data can be downloaded directly to a computer, smartphone, or other smart device, and the user can refer to the downloaded data to track his or her progress. A conventional wearable device may incorporate various sensors to determine activity levels. Examples of such sensors include accelerometers, altimeters, UPS sensors, magnetometers, optical sensors, heart rate sensors, thermometers, and chemical sensors.

Traditionally, athletes and other individuals that run and/or walk for exercise are interested in understanding how to conduct a proper workout for purposes of improved training. While the individual does not want to over-train, the individual also does not wish to under-train such that he or she is not receiving the full benefit of dedicated workout time. Accordingly, it would be advantageous to provide a fitness tracking system that is capable of assisting users of the system in achieving proper workouts that push the individual to a desired extent without overtaxing the body. It would also be advantageous if the system assisted the user in both real-time and over the course of many events. Furthermore, it would be advantageous if such a system included an intuitive and easy-to-understand user interface that communicated workout information to the user in a quick and convenient manner.

SUMMARY

In accordance with one exemplary embodiment of the disclosures, a method of operating a fitness tracking system is disclosed. The method comprises receiving at least one first value for at least one foot action parameter from a sensor coupled to an article of footwear worn by a user at a first time during a user workout, and also receiving at least one second value for the at least one foot action parameter from the sensor coupled to the article of footwear worn by the user at a second time during the user workout. The method further comprises determining a rate of change of the foot action parameter based on the first and second values, and determining whether the rate of change exceeds a threshold rate of change. When the rate of change of the first and second values exceeds the threshold rate of change, a fatigue moment is identified. A recommended action is then determined for the user in response to the fatigue moment. An indication of the fatigue moment and the recommended action is provided to the user via a user interface.

In accordance with another exemplary embodiment of the disclosure, a method of operating a fitness tracking system includes receiving at least one first value for at least one foot action parameter from a sensor coupled to an article of footwear worn by a user at a first time during a user workout, and then receiving at least one second value for the at least one foot action parameter at a second time during the user workout. The method further includes determining whether the user has experienced a first type of fatigue and a second type of fatigue based on the at least one first value and the at least one second value, wherein the first type of fatigue is defined by different rules than the second type of fatigue. When it is determined that the user experienced the first type of fatigue, a first recommended action is provided to the user via a personal electronic device of the user. When it is determined that the user experienced the second type of fatigue, a second recommended action is provided to the user via the personal electronic device, wherein the first recommended action is different from the second recommended action.

In accordance with yet another exemplary embodiment of the disclosure, a fitness tracking system includes a receiver, a display screen, a memory and a processor. The receiver is configured to receive workout data associated with at least one foot action parameter from a sensor device carried by, the user during the user workout. The display screen is provided on a personal electronic device and is configured to display a graphical user interface to the user. The memory is configured to store the workout data. The processor is operably connected to the receiver, the display screen and the memory. The processor is configured to execute program instructions to receive at least one first value for the foot action parameter from the sensor device at a first time during the user workout, receive at least one second value for the foot action parameter from the sensor device at a second time during the user workout, and determine whether the user has experienced a first type of fatigue and a second type of fatigue based on the at least one first value and the at least one second value, the first type of fatigue defined by different rules than the second type of fatigue. When it is determined that the user experienced the first type of fatigue, indicate the first type of fatigue on the graphical user interface and provide a first coaching recommendation to the user via the personal electronic device of the user. When it is determined that the user experienced the second type of fatigue, indicate the second type of fatigue on the graphical user interface and provide a second coaching recommendation to the user via the personal electronic device, wherein the first coaching recommendation is different from the second coaching recommendation.

These and other aspects of the disclosure shall become apparent when considered in light of the disclosure provided herein.

BRIEF DESCRIPTION OF THE DRAWINGS

The above-described features and advantages, as well as others, should become more readily apparent to those of ordinary skill in the art by reference to the following detailed description and the accompanying, figures in which.

Figure 1:
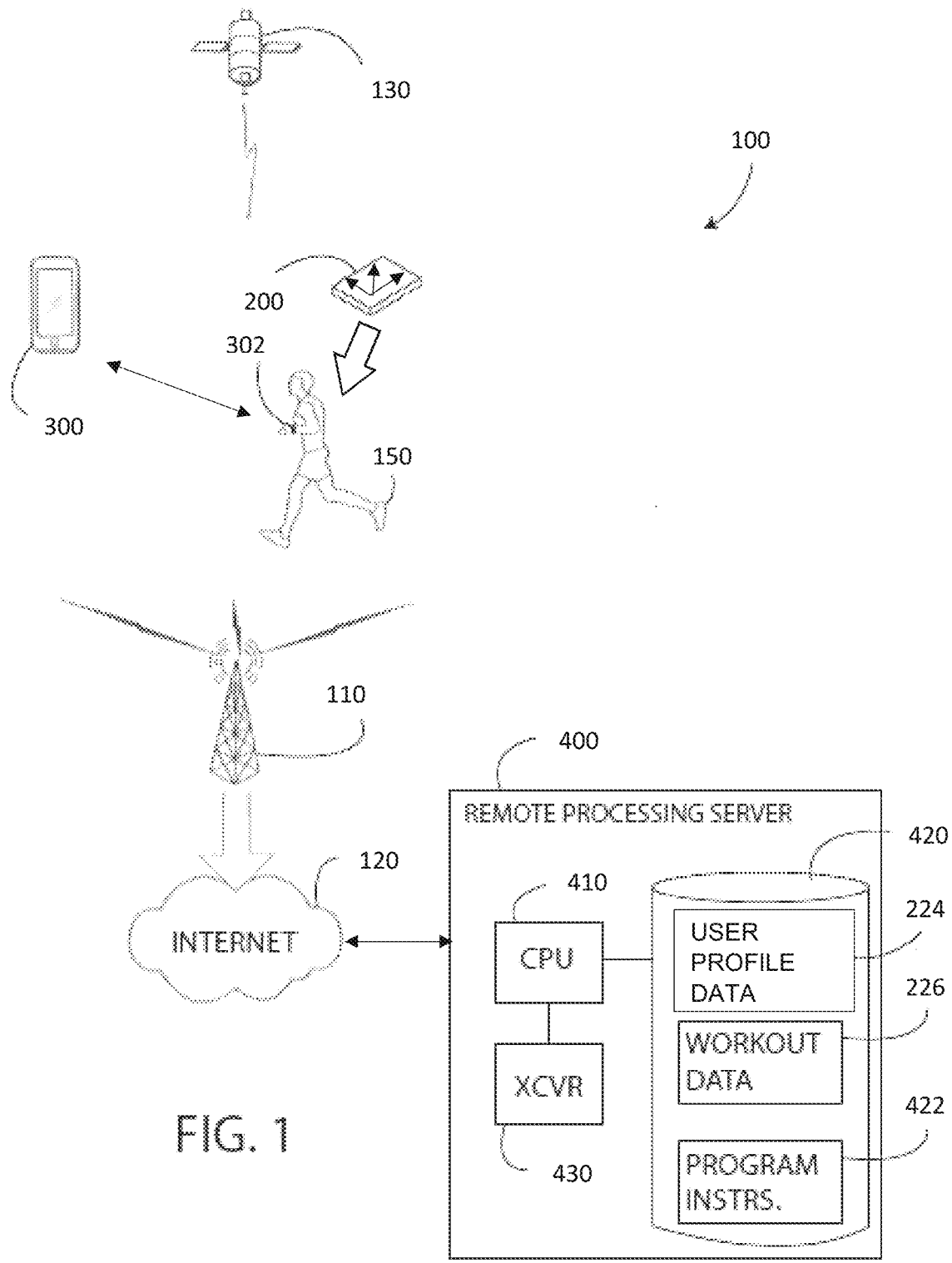
FIG. 1 is a lock diagram of a fitness tracking system, as disclosed herein, that includes a sensor device, a personal electronic device, and a remote processing server.

All Figures © Under Armour, Inc. 2019. All rights reserved.

DETAILED DESCRIPTION

In the following detailed description, reference is made to the accompanying figures which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Additionally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Fitness Tracking System

A fitness tracking system is disclosed herein that is configured to detect user fatigue during a workout. The fitness tracking system is configured to detect fatigue moments for the user as well as fatigue levels for the user over time. User fatigue is monitored within a single workout (i.e., intra-workout) and across a number of different workouts (i.e., inter-workout). Workout recommendations are made to the user based on the detected fatigue moments as well as detected fatigue levels. The workout recommendations may occur during a workout, or after a workout.

As shown in FIG. 1, a fitness tracking system 100 includes a sensor device 200, a personal electronic device 300, and a remote processing server 400. The fitness tracking system 100 (which may alternatively be referred to as an "activity tracking system") collects workout data with the sensor device 200 while an athlete or other user performs a workout, participates in a competition, or otherwise performs some exercise activity. The workout data may include data for any of various workout parameters such as speed, pace, etc. The workout data and other information generated by the system 100 is presented to the user on a personal electronic device 300. As shown in FIG. 1, the various components of the fitness tracking system 100 are in communication with one another via any of various networks, such as personal area networks (e.g., a Bluetooth network), local area networks (e.g., a WiFi network), or a wide area network (e.g., the Internet 120 via a cellular network 110 in communication with the personal electronic device 300, for example). The fitness tracking system 100 may also be configured for use with a global positioning system ("GPS") 130 and one or more GPS devices included with the sensor device 200 or the personal electronic device 300.

The sensor device 200 includes a sensor that is configured to collect workout data for the user. As shown in FIG. 1, the sensor device 200 is configured to be worn or otherwise carried by a user of the fitness tracking system 100. The sensor device 200 may be provided in any number of different forms and configurations. In at least one embodiment described in further detail below, the sensor device 200 is coupled to a shoe 150 worn by the user, such as permanently embedded in the sole of the shoe 150. In other embodiments, the sensor device 200 may be provided in different forms, such as included with the personal electronic device 300, such as a smartphone or a smart watch 302 worn by the user.

Figure 2:
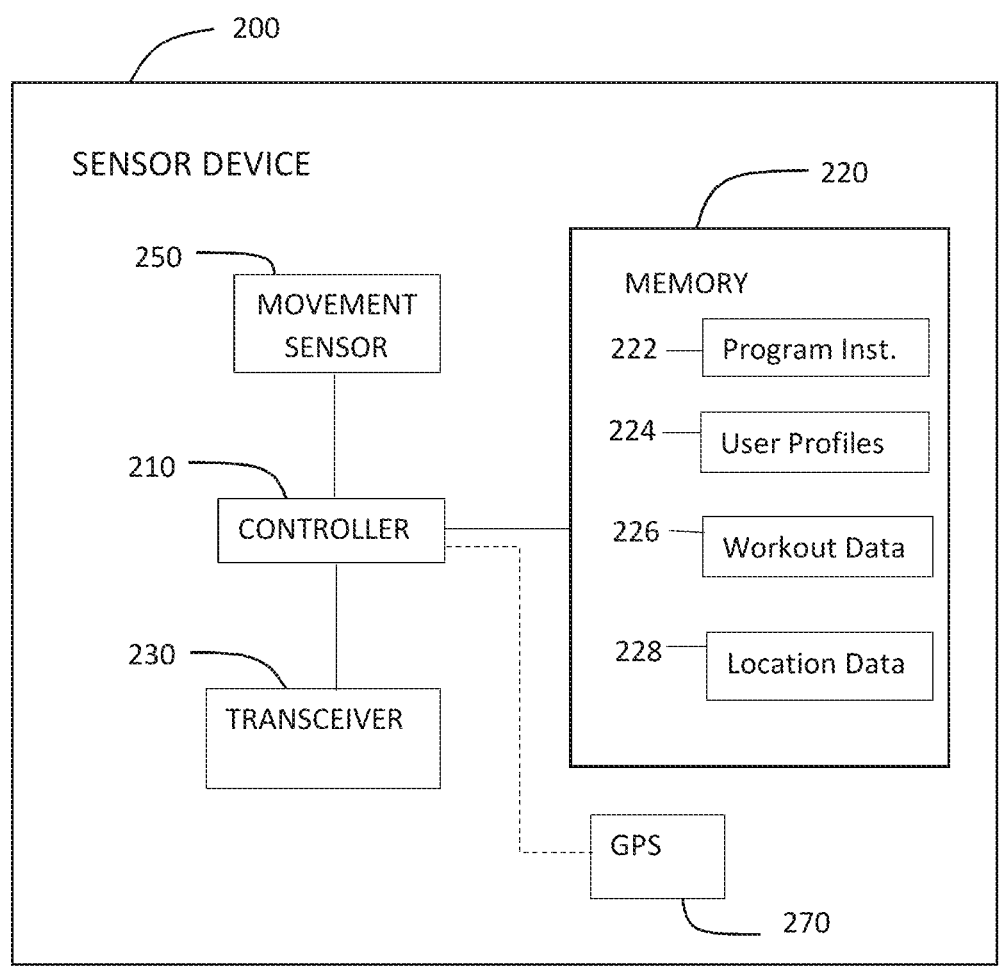
FIG. 2 is a block diagram of the sensor device of FIG. 1.

A block diagram of the sensor device 200 (which may also be referred to herein as a "monitoring device" or "measuring device") is shown in FIG. 2. The sensor device 200 includes a movement sensor 250 (which may also be referred to herein as an "activity sensor"), a transceiver 230, and a memory 220 each of which is operably connected to a controller 210. The movement sensor 250 is configured to collect workout data 226 (which may alternatively be referred to herein as "activity data"), which corresponds to movement of the user during a workout or other exercise session. The movement sensor 250 is provided as any type of sensor configured to generate activity data 226, such as a single-axis or a multi-axis microelectromechanical (MEMS) accelerometer, gyroscope, magnetometer, etc. In at least one embodiment, the movement sensor 250 is an accelerometer and the workout data 226 includes acceleration data corresponding to bipedal movement of the user. Additional workout data 226 such as speed, pace, cadence, ground contact time (GCT), foot strike angle (FSA), stride length, etc. is generated from the acceleration data provided by the sensor. In at least some embodiments, the workout data 226 may also include any of various physiological workout parameters such as heart rate, breathing rate, temperature, etc. Furthermore, the workout data 226 may also include a type of workout associated with the data collected by the sensor, such as a run, walk, cycling, gym workout, etc. Such additional workout data may be determined automatically by the sensor (e.g., using signals from the accelerometer to determine whether the user is walking or running), or may be manually input by the user. The workout data 226 is stored by the controller 210 in the memory 220.

The controller 210 of the sensor device 200 is configured to execute the program instruction data 222 for controlling the movement sensor 250, the transceiver 230, and the memory 220. The controller 210 is provided as a microprocessor, a processor, or any other type of electronic control chip.

The memory 220 of the sensor device 200 is an electronic data storage unit, which may also referred to herein as a non-transient computer readable medium. The memory 220 is configured to store the program instruction data 222, user profile data 224 for the user, and the workout data 226 generated by the movement sensor 250. The program instruction data 222 includes computer executable instructions for operating the sensor device 200, including instructions for collection, generation and transmission of workout data 226. The user profile data 224 includes data specific to the user performing a workout with the sensor device 200. For example, the user profile data 224 may include demographic information about the user such as user age, sex, height, weight, etc. As noted previously, the workout data 226 may include information for any of various workout parameters associated with bipedal movement of the user, such as speed, pace, cadence, ground contact time, foot strike angle, stride length, etc. Such workout parameters that may be derived from movement of the feet of the user may be referred to herein as "foot action parameters." In addition to these foot action parameters, the workout data 226 may include various physiological parameters such as heart rate, breathing rate, temperature, etc., and other parameters derived from sources not associated with the feet of the user, such as global positioning system (GPS) sensors. In any event, because the specific values for the workout parameters change throughout the workout, it will be recognized that the workout data 226 may include specific instances of various parameters (e.g., ground contact time for one stride within the workout) as well as averages for such parameters (e.g., average ground contact time per stride over the course of the workout).

The transceiver 230 of the sensor device 200, which is typically a wireless transmitter and/or receiver, is configured to transmit and to receive data from the personal electronic device 300. In one embodiment, the transceiver 230 is configured for operation according to the Bluetooth® wireless data transmission standard. In other embodiments, the transceiver 230 comprises any desired transceiver configured to wirelessly transmit and receive data using a protocol including, but not limited to, Near Field Communication ("NFC"), IEEE 802.11, Global System for Mobiles ("GSM"), and Code Division Multiple Access ("CDMA").

In at least one embodiment, the sensor device 200 is equipped with a GPS receiver 270. The GPS receiver 270 of the sensor device 200 is configured to receive GPS signals from satellites of the GPS 132 (see FIG. 1). The GPS receiver 270 is further configured to generate location data that is representative of a current location on the Earth of the sensor device 200 based on the received GPS signals. The location data, in one embodiment, includes latitude, longitude, and elevation information. The controller 210 is configured to store the location data generated by the GPS receiver 270 in the memory 220 as part of the workout data 226.

Figure 4:
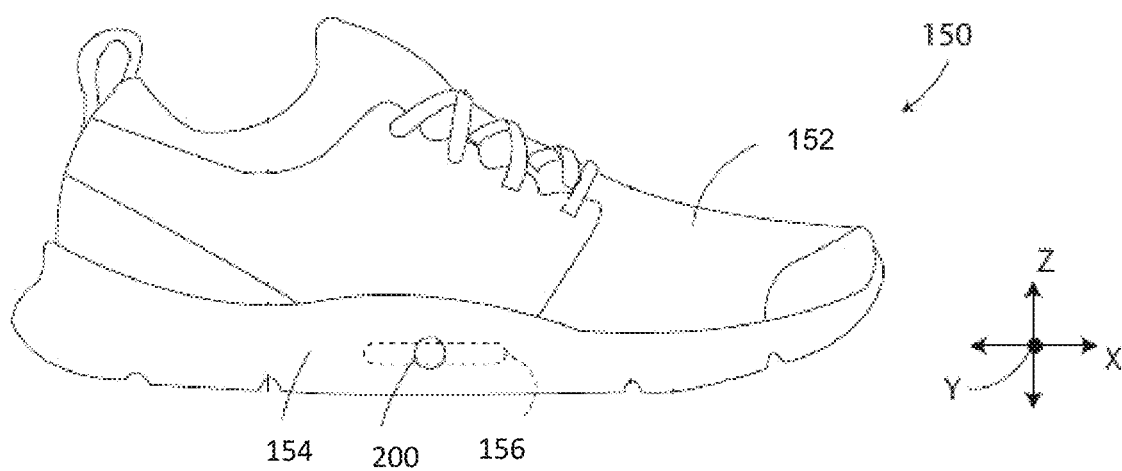
FIG. 4 is a side elevational view of a shoe including the sensor device of FIG. 1.

With reference now to FIG. 4, in at least one embodiment, the sensor device 200 is provided on a shoe 150 worn by the user. Accordingly, the user is equipped to carry the sensor device 200 during the workout by simply donning the shoe 150. The shoe 150 includes an upper 152 and a sole 154. The sensor device 200 may advantageously be embedded within a pocket 156 provided within the sole. For example, as shown in FIG. 4, the sensor device 200 may be arranged within a midsole of the shoe 150 such that the foam or other polymer material that provides the midsole encompasses the sensor device 200. As noted by the legend 160, the sensor device 200 is configured to detect movement of the shoe in three dimensions.

While the sensor device 200 is shown in FIG. 4 embedded within the sole 154 of the shoe 150, it will be recognized that in alternative embodiments, the sensor may be positioned at other locations in or on the shoe 150, or may even be disassociated with the shoe. For example, the sensor device 200 may be alternatively configured for placement in or on the tongue or other location on the shoe 150. In still other embodiments, the sensor device 200 may be a completely separate component from the user's shoes. For example, the sensor device 200 may be a standalone device or may be included with the user's personal electronic device 300. In such embodiments, the sensor device is carried by the user in some manner, such as by hand, included with a garment worn by the user, or inserted in a pocket of the user's clothing or coupled to an accessory worn the user (e.g., wrist strap, clip, band, hat, eyeglasses, necklace, visor, etc.). Moreover, in some embodiments, multiple sensor devices may be used to collect activity data, such as a sensor device in a shoe and a sensor device on a watch, or a left sensor device located and/or affixed to the user's left shoe, and a right sensor device located and/or affixed to the user's right shoe.

The sensor device 200 is in communication with the personal electronic device 300, as shown in FIG. 1. The personal electronic device 300 is configured to receive data from the sensor device, process such data, and provide a user interface for the processed data. In at least one embodiment, the exemplary personal electronic device 300 is configured as a smartphone. In other embodiments, the personal electronic device 300 is provided as a smartwatch, an electronic wristband, earbuds, headphones, a tablet computer, a desktop computer, or the like. It will be recognized that in some embodiments the personal electronic device 300 is portable and configured to be worn or otherwise carried by the user and may communicate with the sensor device 200 during a workout or other exercise session. In other embodiments, the personal electronic device 300 is not portable, and the personal electronic device 300 may only receive the activity data 226 from the sensor device 200 after the user completes an exercise session.

Figure 3:
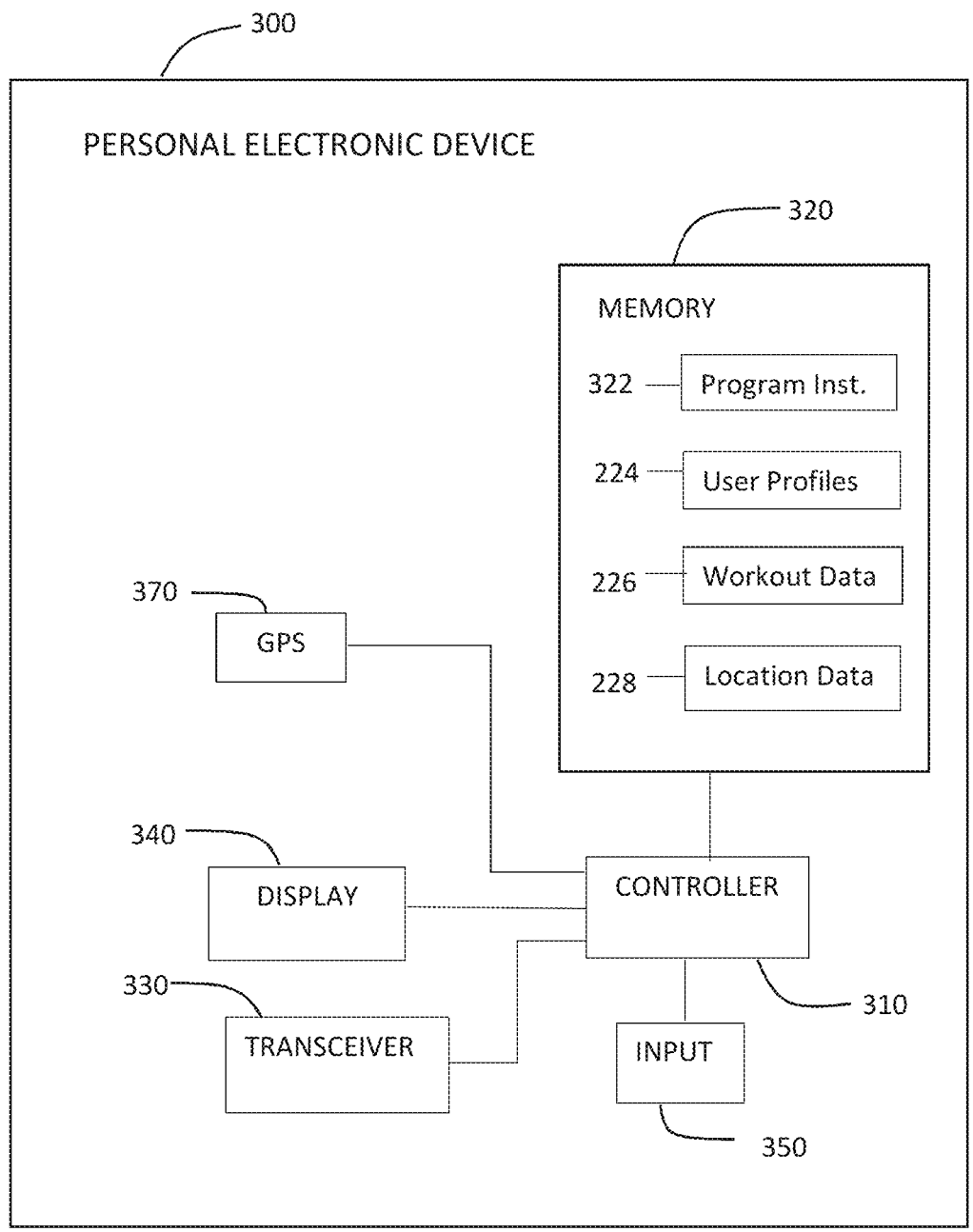
FIG. 3 is a lock diagram of the personal electronic device of FIG. 1.

With particular reference now to FIG. 3, the personal electronic device 300 includes a memory 320, a transceiver 330, a display 340, an input unit 350, and a GPS receiver 370, each of which is operably connected to a processor or a controller 310. In at least one embodiment, the personal electronic devices is a smartphone, smart watch, tablet computer, or other portable electronic device. However, it will be recognized, that the personal electronic device 300 may also be provided in other forms, such as a standalone personal computer.

As shown in FIG. 3, the memory 320 of the personal electronic device 300 is an electronic data storage unit, which may also be referred to herein as a non-transient computer readable medium. The memory 320 is configured to store electronic data associated with operating the personal electronic device 300 and the sensor device 200, including program instruction data 322, workout data 226, and user profile data 224.

The program instruction data 322 includes computer executable instructions for controlling the personal electronic device. For example, the program instructions 322 may include computer executable instructions for generating the workout data 226 based on signals received from the sensor device 200. As explained in further detail below, the program instructions 322 include both a fatigue identification engine and a coaching engine. The fatigue identification engine is configured to analyze workout data and determine whether a user is fatigued. One example of a system configured to detect user fatigue is provided in U.S. Pat. No. 10,251,596, issued Apr. 9, 2019, the contents of which are incorporated herein by reference.

In addition to detecting whether a user is fatigued or not fatigued, the fatigue identification engine disclosed herein is also configured to determine whether a user experienced one or more of a number of different types of fatigue. A "type of fatigue" as used herein refers to a category of fatigue based on a particular set of calculations or rules that define the fatigue. Accordingly, different types of fatigue, as used herein, do not simply refer to the existence or non-existence of fatigue, or one of a number of different fatigue values. Instead, the term "type of fatigue" (or "fatigue type") refers to one of a number of different categories of fatigue, each category being defined by different characteristics, parameters, guidelines or other rules. For example, a first type of fatigue that may be determined by the system is a "fatigue moment" where the user has "hit the wall." In this situation, the fatigue moment is identified based on a rate of change of one of the workout parameters (e.g., the rate of change of user cadence exceeds some threshold rate of change). It will be recognized that a fatigue moment is not dependent solely on a value of the workout parameter (or parameters), but is instead based on the rate of change of the parameter (or parameters). As another example, a second type of fatigue that may be determined by the system is that the user has experienced a change in a "fatigue level" based on a value for a workout parameter (or parameters) crossing some threshold (e.g., the value for cadence crosses a predetermined threshold for the user). Thus, it will be recognized that, unlike a fatigue moment, a fatigue level is not dependent on the rate of change of a workout parameter (or combination of parameters), but is instead dependent only on a present value for the parameter (or combination of parameters). Thus, a "fatigue moment" is a different type of fatigue than a "fatigue level." Additional disclosure and examples of rules for defining different types of fatigue are disclosed in further detail below.

With continued reference to FIG. 3, after the fatigue identification engine has determined a type of fatigue for the user, the coaching engine may be used to provide appropriate coaching for the user for delivery via the personal electronic device 300. Methods employed by the fatigue identification engine and the coaching engine are provided below under the headings entitled "fatigue identification engine" and "coaching engine." While the fatigue identification engine and the coaching engine are described herein as being provided on the personal electronic device 300, it will be recognized that in other embodiments the fatigue identification engine and the coaching engine may be provided on other devices, such as the remote processing server 400, and the relevant workout data, coaching instructions, or other data may be shared between the devices.

With continued reference to FIG. 3, the workout data 226 stored on the personal electronic device 300 includes data related to each workout performed by the user when carrying the sensor device 200. As noted previously, the workout data 226 includes a number of different workout parameters and associated values that define each workout. For example, the workout parameters may include type of workout (e.g., run, walk, bike, etc.), time, distance traversed, speed, pace, cadence, stride length, heart rate, stride length, ground contact time, ground contact time percentage, foot strike pattern, efficiency, movement quality, fatigue index, power output, or any of various additional workout parameters and values, including cumulative values, average values (such as mean, median or mode), instantaneous or split-time values within the workout for any of such parameters. Values for such parameters may be calculated based on the signals from the sensor device 200 using any of various known methods, as will be recognized by those of ordinary skill in the art.

In addition to data for a single workout, the workout data 226 may further include cumulative workout data for a group of workouts performed over a period of time. For example, the workout data 226 may include a total or an average parameter value for a group of run-type workouts performed within the past week or month. Exemplary cumulative workout data includes a total distance traversed over a period of time, an average distance per workout, an average speed/pace for the group of workouts, etc. The above-referenced parameters are exemplary, and the controller 310 and/or the controller 210 may be configured to perform any of various calculations using the workout data 226 in order to arrive at the cumulative workout data. The workout data 226 may be limited to workout data performed by the user within a given period of time (e.g., within the past year), or may include all workout data ever generated for the user on the personal electronic device 300.

As noted previously, the user profile data 224 is based on demographic information of the user and may include one or more of various demographic identifiers for the user such as gender, height, weight, body mass index ("BMI"), age, body fat percentage, resting heart rate, and other data. Any other user demographic and/or physiological data may be included in the demographic data/user profile data 224. For example, the demographic data could further include, experience level of the runner or other athlete (e.g., years running, races run, etc.), estimated VO2 max, lactate/anaerobic threshold, etc. The user profile data 224 may also be referred to herein as "demographic data."

With continued reference to FIG. 3, the transceiver 330 of the personal electronic device 300 is configured to wirelessly communicate with the transceiver 230 of the sensor device 200 and the remote processing server 400. The transceiver 330 wirelessly communicates with the remote processing server 400 either directly or indirectly via the cellular network 110 (FIG. 1), a wireless local area network (e.g., a Wi-Fi network), a personal area network (e.g., a Bluetooth network), and/or any other wireless network. Accordingly, the transceiver 330 is compatible with any desired wireless communication standard or protocol including, but not limited to, Near Field Communication ("NFC"), IEEE 802.11, Bluetooth®, Global System for Mobiles ("GSM"), and Code Division Multiple Access ("CDMA"). To this end, the transceiver 330 is configured to transmit data to and receive data from both the remote processing server 400 and the sensor device 200. Accordingly, the transceiver may be considered to include both of a transmitter and a receiver for accomplishing such data reception and transmission.

The display 340 of the personal electronic device 300 may comprise a liquid crystal display (LCD) panel configured to display static and dynamic text, images, and other visually comprehensible data. For example, the display 340 is configurable to display one or more interactive interfaces or display screens to the user including a display of workout data and related data collected during one or more user workouts.

The input unit 350 of the personal electronic device 300 is configured to receive data input via manipulation by a user. For example, the input unit 350 may be configured as a touchscreen applied to the display 340 that is configured to enable a user to input data via the touch of a finger and/or a stylus. In another embodiment, the input unit 350 comprises any device configured to receive user inputs, as may be utilized by those of ordinary skill in the art, including, e.g., one or more buttons, switches, keys, and/or the like.

The GPS receiver 370 of the personal electronic device 300 is configured to receive GPS signals from satellites of the GPS 132 (see FIG. 1). The GPS receiver 370 is further configured to generate location data 228 that is representative of a current location on the Earth of the personal electronic device 300 based on the received GPS signals. The location data 228, in one embodiment, includes latitude, longitude, and elevation information. The controller 310 is configured to store the location data 228 generated by the GPS receiver 370 in the memory 320. The location data 228 may also be referred to herein as "GPS data." It will be appreciated that the GPS receiver 370 is typically absent from embodiments wherein the personal electronic device 300 is not a portable device.

The controller 310 of the personal electronic device 300 is configured to execute the program instruction data 322 in order to control the components of the personal electronic device 300, including the memory 320, the transceiver 330, the display 340, the input unit 350, and the GPS receiver 370. The controller 310 is provided as a microprocessor, a processor, or any other type of electronic control chip. The controller 310 is configured to receive workout data 226 from the sensor device 200 via the transceiver. The controller 310 is also configured to workout data in the form of user location data via the GPS unit 370. The controller 310 is further configured to process the workout data 226 and generate additional workout data by applying various rules to the received workout data. For example, as discussed in further detail below, the controller 310 is configured to determine different types of user fatigue, including various fatigue moments based on the received workout data.

Although the sensor device 200 and the personal electronic device 300 are described generally herein as completely separate devices, each with its own processor and housing, it will be recognized that in at least some embodiments, the sensor device 200 may be part of the personal electronic device 300. In such embodiments, the components of the sensor device 200 are commonly housed with the personal electronic device 300, and certain components may be shared, such as a shared processor. When the sensor device 200 and the personal electronic device are provided in a common housing, both devices are intended to be carried by the user during workouts. Alternatively, if the personal electronic device 300 is housed separate from the sensor device, the personal electronic device 300 may be left behind or remote from the user during such workouts and other activities. In any event, when the personal electronic device 300 is carried by the user along with the sensor device 200, data from the sensor device 200 may be periodically sent to the personal electronic device 300 during workouts and other activities. On the other hand, if the personal electronic device 300 is not carried by the user during a workout, data from the sensor device 200 may be uploaded to the personal electronic device 300 at the end of a workout when the two devices are in sufficiently close proximity for communication.

With reference again to FIG. 1, it will be recognized that the fitness tracking system 100 may also include a remote processing server 400. The remote processing server 400 is remotely located from the sensor device 200 and the personal electronic device 300. That is, the server 400 is located in a first physical location and the personal electric device 300 and the sensor device 200 are located in a second physical location that is different from the first physical location. The server 400 is configured to receive the workout data 226 from the personal electric device 300 via the Internet 120 and store the workout data. To this end, the server 400 includes a central processing unit 410, a memory 420, and a transceiver 430. Each of the memory 420 and the transceiver 430 are operably connected to the central processing unit 410.

The memory 420 of the remote processing server 400 includes program instructions 422, as well as copies of the user profile data 224 and the workout data 226. The server 400 is configured to receive the user profile data 224 and the workout data 226 and store backup copies of the data. The backup copies of the data stored at the remote processing server 400 may include historical copies of data from user workouts that occurred over the course of many months or many years. In contrast, only limited amounts of data may be stored on the personal electronic device 300 or the sensor device 200, such as days, weeks or months of data. Moreover, the central processing unit 410 of the remote processing server 400 may be configured to generate additional workout data not previously generated by the other components of the system. Accordingly, it will be recognized that the remote processing server 400 may be used as a backup storage location as well as either a primary or secondary processing location for the workout data 226. In some embodiments of the fitness tracking system 100, all of the workout data is generated on the personal electronic device 300 without the user of the remote processing server. In other embodiments, at least some of the workout data is generated on the remote processing server 400.

The transceiver 430 of the remote processing server 400 is configured to wirelessly communicate with the personal electronic device 300 either directly or indirectly via the cellular network 110, a wireless local area network ("Wi-Fi"), a personal area network, and/or any other wireless network. Accordingly, the transceiver 430 is compatible with any desired wireless communication standard or protocol including, but not limited to, Near Field Communication ("NFC"), IEEE 802.11, Bluetooth®, Global System for Mobiles ("GSM"), and Code Division Multiple Access ("CDMA").

Fatigue Identification Engine

As noted above, the fitness tracking system 100 includes a fatigue identification engine and a coaching engine included within the program instructions 322. The fatigue identification engine is configured to receive workout data and determine different fatigue types that may have been experienced by the user during one or more workouts. In particular, the fitness tracking system 100 is configured to make use of the workout data provided by the sensor device 200 and determine the occurrence of "fatigue moments" during the workout as well as a "fatigue level" at any given time during the workout. As noted previously, a "fatigue moment" is defined by a different set of rules than a "fatigue level." In particular, a fatigue moment is indicative of a period during a workout when the user experienced a significant rate of change in one or more workout variables. On the other hand, a fatigue level is an indication of a relative amount of fatigue for the user, and may be presented as a continuous or discrete variable. For example, the fatigue level may be a continuous variable between 1.0 and 10.0, any of various words such as "low," "mid," or "high" fatigue, and any of various colors associated therewith. Alternatively, the fatigue level may be a discrete variable such as the word "yes" to indicate fatigue or the word "no" to indicate no fatigue. Based on the various determinations of fatigue type, including both fatigue moments and fatigue level, the coaching engine is configured to provide improved coaching to the user, wherein the coaching is dependent at least in part on the existence of various fatigue moments and/or various fatigue levels for the user during one or more workouts. As will be explained below, the coaching provided by the system 100 may occur either during or after a workout, and may be applicable to only a single workout or across a number of different workouts. Additionally, although the fatigue identification engine and the coaching engine have been identified as being including within the program instructions 322 of the personal electronic device 300, it will be recognized that one or more of the fatigue identification engine and the coaching engine may be provided on other devices (e.g., included with the program instructions 222 of the sensor device 200, or included with the program instructions 422 of the remote processing server 400).

Figure 5:
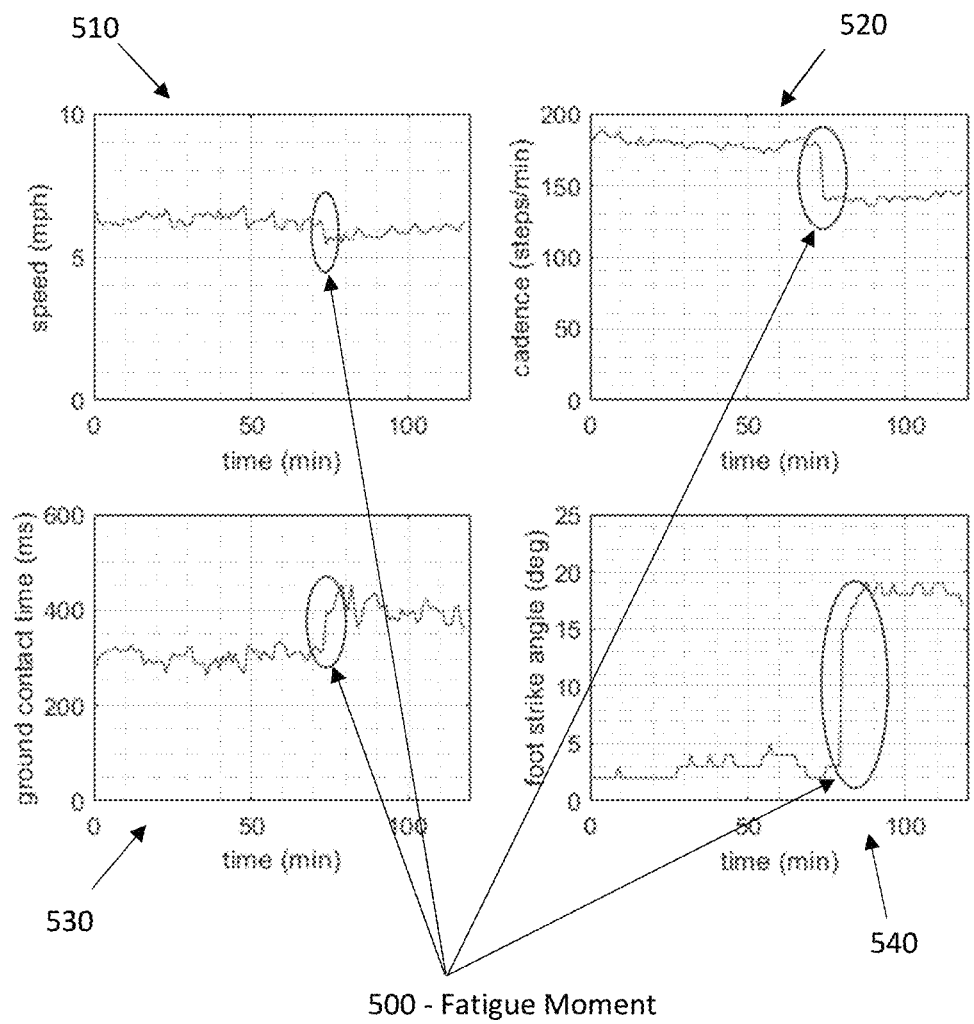
FIG. 5 shows four charts of parameters for workout data for a first user workout associated with a fatigue moment.
Figure 6:
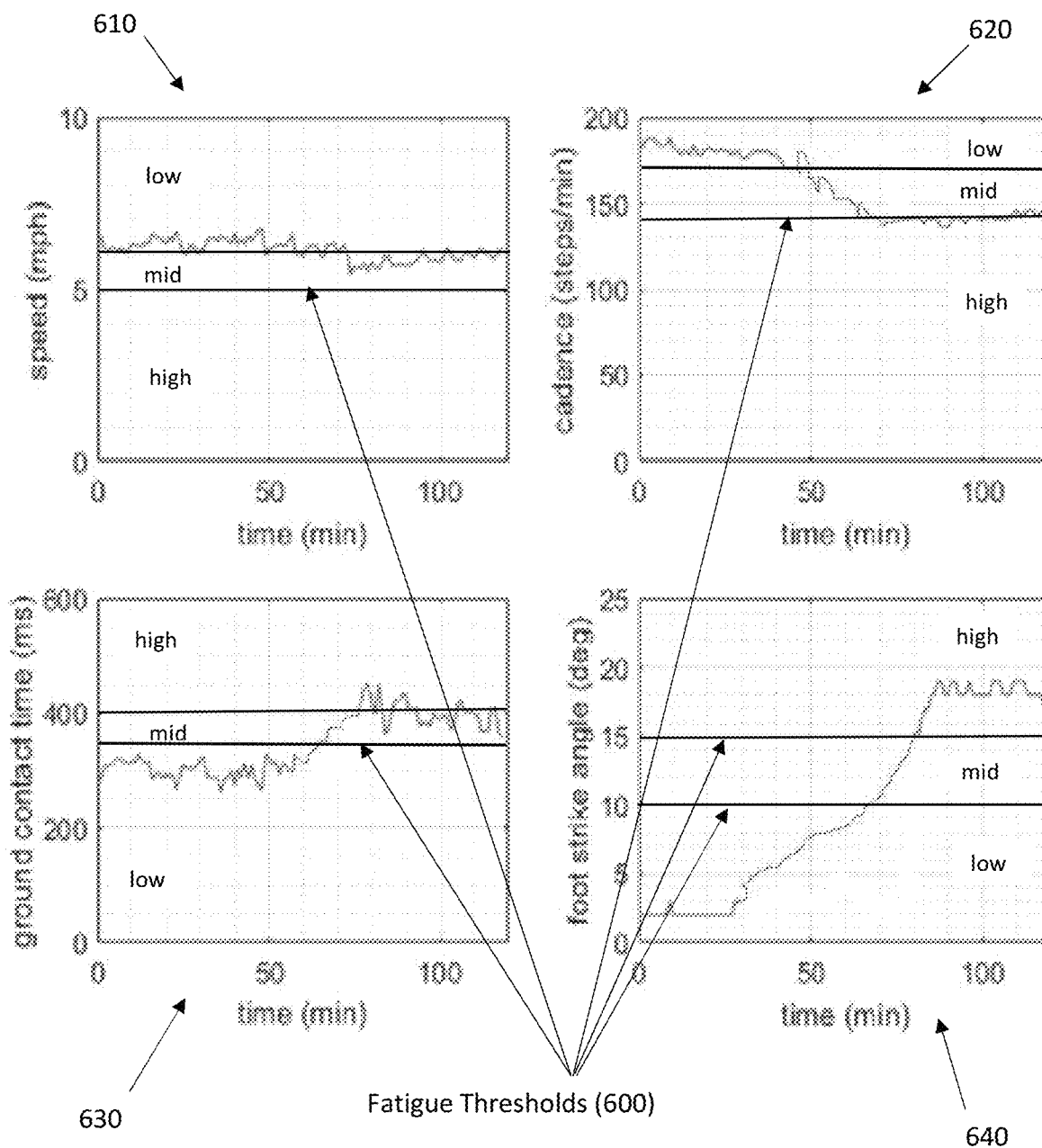
FIG. 6 shows four charts of parameters for workout data for a second user workout associated with a more gradual onset of fatigue.
Figures 7, 8:
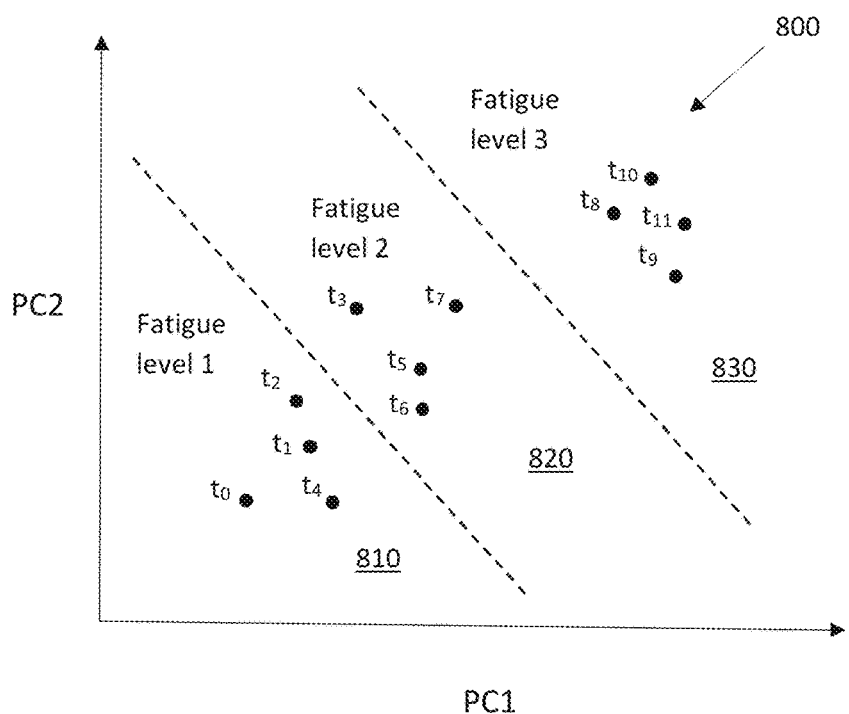
FIG. 7 is a table showing values for the workout data of FIG. 5.
FIG. 8 is a PCA plot of the workout data of FIG. 7 with the workout data clustered based on fatigue level.

At least one embodiment of a method used by the fatigue engine to determine different types of fatigue is described now with reference to FIGS. 5-8. FIG. 5 represents workout data wherein a fatigue moment is identified. FIG. 6 represents workout data wherein more gradual fatigue occurs and various fatigue levels are identified. FIGS. 7 and 8 represent the use of a dimensionality reduction method in order to determine various fatigue levels based on the workout data of FIG. 5.

With particular reference now to FIG. 5, four graphs of exemplary workout data are shown for a first run of the user wherein the user experienced a fatigue moment. The user of the fitness tracking system 100 performed the first run while carrying the sensor device 200. For example, the user may have worn the shoe 150 of FIG. 4 with an embedded sensor device, worn a smartwatch, or carried a smartphone or other personal electronic device 300 on a garment worn by the user. The four graphs of FIG. 5 show workout data for the user during a two-hour (120 minute) run. The workout data includes four different workout parameters collected during the run, including speed (in mph as noted in graph 510), cadence (in steps/min as noted in graph 520), ground contact time (in milliseconds as noted in graph 530), and foot strike angle (in degrees as noted in graph 540). The workout data shown in the graphs includes data that is representative of a fatigue moment 500 experienced by the user during the first workout.

As shown by the data in the graphs 510, 520, 530 and 540 of FIG. 5, each of the four parameters remains relatively steady for the first half of the workout, prior to a fatigue moment 500 wherein the user "hits the wall." For example, the user's speed during the first hour of the workout remains generally around 6.4 mph (as noted in graph 510). Similarly, the users, cadence during the first hour remains around 180 steps per minute (as noted in graph 520), the user's ground contact time (GCT) remains around 300 ms (as noted in graph 530), and the user's foot strike angle (FSA) remains between 2° and 4° (as noted in graph 540). However, between minute seventy (70) and eighty (80) of the workout, significant changes occur in several of the workout parameters over a short period of time. In particular, within a few minutes of time, the user's cadence drops from 180 to about 140 steps/minute (i.e., a rate of change between 20 and 40 (steps/minute)/minute); the user's GCT rises from about 300 ms to more than 400 ms (i.e., a rate of change between 50 and 100 ms/minute); and the user's foot strike angle rises from 2 or 3° degrees to 18 or 19° (i.e., a rate of change between 8 and 14 deg/minute). During this same time, speed changes only slightly from about 6 mph to about 5.5 mph (i.e., a rate of change between about 0.25 to 0.5 mph), but the rate of change is not as significant as the other three workout parameters. It will be recognized that the graphs of FIG. 5 are illustrative of only one particular example of values for one workout from one particular user, and are not necessarily representative of typical fatigue parameters (e.g., in this example, the user's cadence fell to an unusually low level for a run).

The fatigue identification engine monitors the rate of change of the workout parameters and identifies a fatigue moment 500 when the rate of change of one or more of the parameters is in excess of a threshold or otherwise indicative of a fatigue moment. Identification of the fatigue moment may be based on only one or a combination of the workout parameters (e.g., one or more of cadence, GCT, FSA, etc.). Additionally, identification of the fatigue moment may also be based on such parameters exceeding one or more predetermined rate of change thresholds for such parameters. In various embodiments, the predetermined rate of change thresholds are based on a number of different factors, such as the demographic information for the user in the user profile as well as historical workout data for the user. Therefore, in addition to taking into consideration the user's age, sex, weight, etc., the fatigue identification engine may also consider historical workout data for the user when determining a rate of change threshold that is indicative of a fatigue moment. In at least one embodiment, the rate of change threshold is for a rate of change that occurs over a minimum period of time (e.g., one minute or more). In this manner, bad data or brief changes in the workout data that may be indicative of a user encountering some difficulty other than fatigue (e.g., the user entering a crowded area, a change of running surface, etc.) is not used to falsely indicate fatigue of the user.

In the example workout data shown in FIG. 5, the fatigue threshold engine determines that the user encountered a fatigue moment 500 near minute seventy-one of the workout, because this is the time when the rate of change for at least three of the workout parameters (i.e., cadence, GCT and FSA) exceeded their respective rate of change thresholds. In various embodiments of the fatigue threshold engine, a rate of change in excess of the threshold for one workout parameter may be given greater weight than that of another workout parameter. For example, in one embodiment, the rate of change of the user's GCT is weighted more than the rate of change of the user's cadence. In at least one embodiment, a dimensionality reduction method such as principal component analysis is applied to a plurality of the workout parameters in order to create one or more new workout parameters that are then analyzed to determine whether the user experienced a "fatigue moment." Accordingly, it will be recognized that any of various method may be used to determine a fatigue moment using the fitness tracking system 100.

With reference now to FIG. 6, four graphs of exemplary workout data are shown for a second run of the user wherein the user experienced the gradual onset of fatigue, but did not experience a particular fatigue moment. Similar to FIG. 5, the workout data of FIG. 6 includes four different workout parameters collected during the run, including speed (in mph as noted in graph 610), cadence (in steps/min as noted in graph 620), ground contact time (in ms as noted in graph 630), and foot strike angle (in degrees as noted in graph 640).

As illustrated in FIG. 6, the fatigue identification engine includes a plurality of fatigue thresholds 600 that are indicative of various levels of fatigue (e.g., low, mid and high fatigue) specific to the user. In the embodiment of FIG. 6, each of the workout parameters includes two thresholds: a low-to-mid threshold, and a mid-to-high threshold. Accordingly, in this embodiment, the fatigue identification engine is configured to determine one of three fatigue levels for the user: low, mid and high. However, it will be recognized that any number of different fatigue levels are possible, including only two levels (i.e., fatigue or no fatigue), and also including a finite range of fatigue levels (e.g., a level between 1.0 and 10.0, such as 5.7). Moreover, similar to the fatigue moment thresholds discussed in association with FIG. 5, it will be recognized that in at least some embodiments, the various fatigue level thresholds are given different weights based on the associated workout parameters. Moreover, fatigue level thresholds may not necessarily be associated with individual workout parameters, and may instead be associated with combinations of workout parameters, such as when a dimensionality reduction method is used to determine fatigue status. Additionally, it will be recognized that the fatigue level thresholds of FIG. 6 are based on a number of different factors, such as the demographic information for the user in the user profile as well as historical workout data for the user. Therefore, in addition to taking into consideration the user's age, sex, weight, etc., the fatigue identification engine may also consider historical workout data for the user when determining a threshold that is indicative of a different level of fatigue for the user.

As shown by the data in the graphs 610, 620, 630 and 640 of FIG. 6, each of the four parameters remains relatively steady for the first forty minutes of the workout, prior to the gradual onset of fatigue. Starting near minute forty or fifty, the gradual onset of fatigue begins and phases through the three levels: initially at no/low-level fatigue, then to mid-level fatigue, and finally to high-level fatigue. As shown in the figures, each of the user's speed, cadence, GCT and FSA gradually changes between minutes forty and seventy, as the user experiences the gradual onset of fatigue during this period of time. The fatigue identification engine monitors the various workout parameters for the user and identifies a level of fatigue for the user at various times during the workout (e.g., once every minute, 15 seconds, etc.). In the example workout data shown in FIG. 6, the fatigue threshold engine determines that the user experienced low fatigue until minute fifty, experienced mid-level fatigue between minutes fifty and eighty, and high-level fatigue starting around minute eighty. This determination is made based on an analysis of the thresholds for each of the four workout parameters and their associated fatigue thresholds, and not based on any one of the workout parameters. Thus, even though the user's speed never crosses the mid-to-high fatigue threshold in FIG. 6, the fatigue identification engine nevertheless determines that the user is at a high fatigue level based on the other three workout parameters (i.e., cadence, GCT and FSA) exceeded their respective rate of change thresholds.

While speed was specifically mentioned as a workout parameter used to detect speed in the foregoing example, it will be recognized that different workout parameters, or combinations thereof, may be used to determine fatigue levels in different embodiments of the system. For example, in at least one embodiment, a user speed is not used to determine fatigue levels. In such an embodiment, the fitness tracking system may utilize a set of workout parameters that does not include speed in order to determine a fatigue level, and then encourage the user to manage the distance or duration of their workout and/or better manage their biomechanics (i.e., foot action parameters) to avoid a reduction in speed.

With reference now to FIGS. 7 and 8, an example of an embodiment of the fatigue identification engine configured to analyze a plurality of workout parameters in order to detect fatigue levels or fatigue moments for the user is shown. This embodiment of the fatigue identification engine implements a dimensionality reduction method in order to convert the correlations between data points into more easily understandable two-dimensional space, thus allowing the system to make a determination concerning fatigue at any given point in time during the workout.

FIG. 7 shows a table 700 of workout data from a user workout. The values for the workout data shown in the table 700 are taken from the workout data illustrated in the graphs of FIG. 5. Accordingly, as shown in the table 700, four workout parameters are included in the table: speed, cadence, GCT and FSA. The table 700 also includes values for each workout parameter at twelve different times during the workout (i.e., times $t_0$-$t_{11}$, which correlate to the start of the workout and snapshot of the data every ten minutes thereafter). It will be recognized that while the table 700 shows only twelve data points, in practice all data points collected during a workout, or a significantly greater number of data points are analyzed by the fatigue identification engine. The fatigue identification engine operates using a set of rules that may incorporate a dimensionality reduction method, such as principal component analysis (PCA), in order to analyze the workout data and determine a fatigue level for the user and/or a fatigue moment for any given data point.

FIG. 8 shows a PCA plot 800 of the workout data (e.g., the workout data of table 700). Advantageously, the PCA plot 800 converts the correlations (or lack thereof) among the workout data into a two-dimensional graph of data points. The horizontal axis is the first principle component axis (PC1) and the vertical axis is the second principle component axis (PC2). In at least one embodiment, PC1 is a first new workout parameter that is representative of two of the workout parameters that are more associated with fatigue (e.g., cadence and FSA), and PC2 is a second new workout parameter that is representative of two other workout parameters that are slightly less associated with fatigue (e.g., speed and GCT). Thus, in at least some embodiments, the fatigue identification engine weighs the PC1 more heavily than PC2 for the purposes of determining fatigue. In such an embodiment, the further a cluster is to the right on the PCA plot 800, the more likely that this data point is representative of a higher level of user fatigue.

The result of the PCA plot 800 is that various data points are organized into clusters on the plot. Based on the location of the clusters on the PCA plot 800, the fatigue identification engine determines that the data points in each cluster are indicative of various fatigue levels (or fatigue moments). For example, in the embodiment of FIG. 8, the PCA plot is split into three fatigue regions, including a first region 810 associated with a first fatigue level, a second region 820 representative of a second fatigue level, and a third region 830 representative of a third fatigue level. The fatigue regions on the PCA plot 800 may be unique to the individual user and may be based on a priori data, a posteriori data, or some combination thereof. For example, the fatigue regions 810, 820, 830 identified on the PCA plot may be based at least in part on demographic data (e.g., age, sex, weight, etc.) or other a priori data. Additionally, the fatigue regions 810, 820, 830 may be based on empirical data for the user such as fatigue data from past workouts. Moreover, as noted previously, the three fatigue regions on the PCA plot 800 of FIG. 8 are representative of only one embodiment wherein the fatigue identification engine determines three fatigue levels, and any number of fatigue levels are possible, including two discrete fatigue levels, or fatigue levels that are continuous over a range of fatigue values (e.g., 1-10). Also, as noted previously, in addition to the fatigue identification engine using principal component analysis to determine fatigue levels, the fatigue identification engine may similarly use principal component analysis to determine fatigue moments.

While a dimensionality reduction method such as principle component analysis has been described herein as one possible tool used by the fatigue identification engine to identify new workout parameters and arrive at values for different fatigue types, including fatigue levels and fatigue moments, it will be recognized that the use of other tools is possible. For example, as discussed previously herein, the fatigue identification engine may analyze one or more of the workout parameters over time in order to determine a fatigue level or fatigue moment for the user. As another example, the fatigue identification engine may use an equation that assigns a weight to each value for the individual workout parameters and arrives at a fatigue score for the user. Thereafter, based on the fatigue score, a fatigue level or fatigue moment may be identified by the fatigue identification engine. Accordingly, it will be recognized that the fatigue identification engine in the fitness tracking system 100 may make use of any of various tools and rules for arriving at a fatigue determination for a user during a workout.

Coaching Engine

Figure 9:
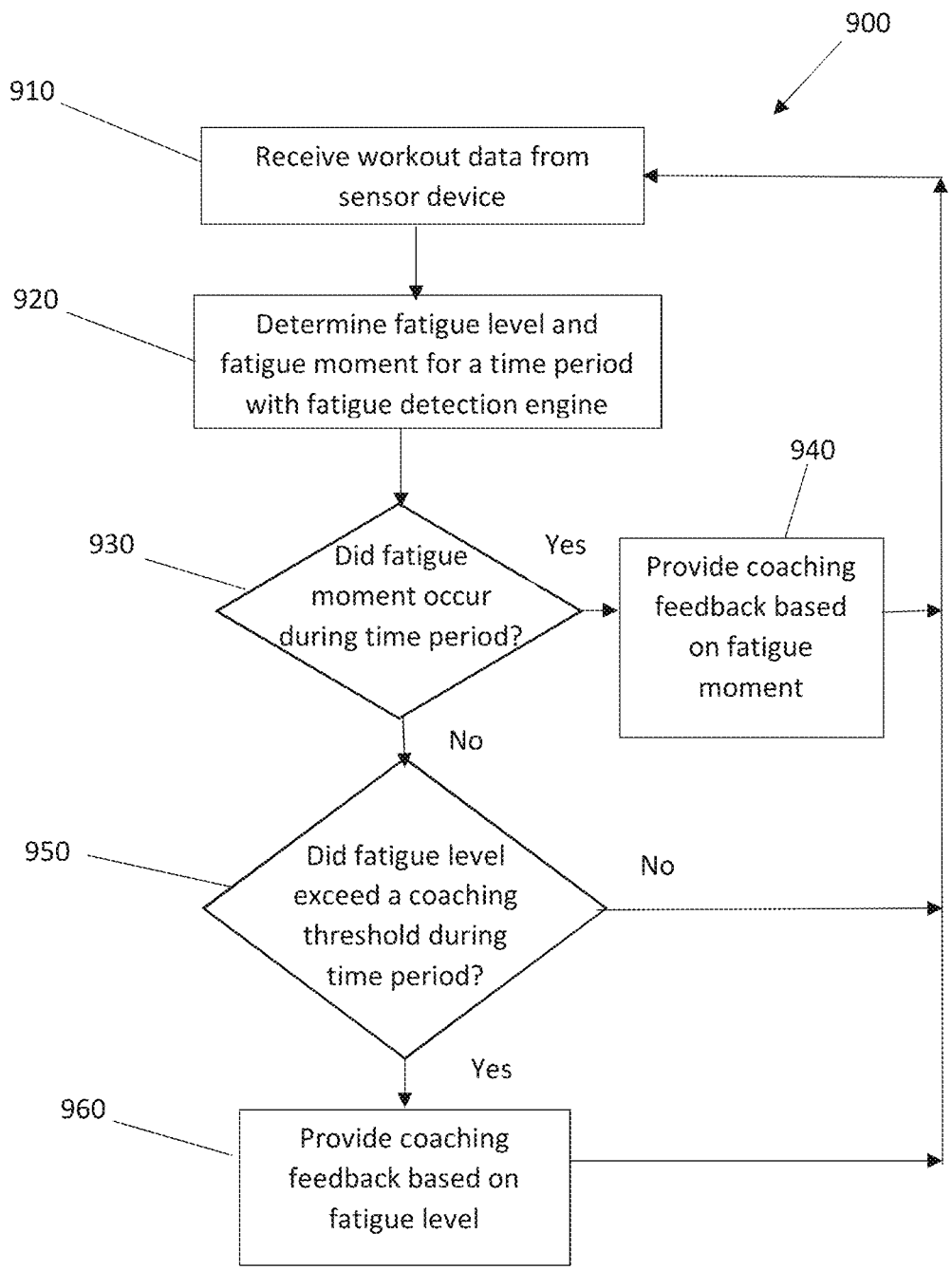
FIG. 9 is a flowchart illustrating an exemplary method of operating a fatigue identification engine and a coaching engine of the fitness tracking system shown in FIG. 1.

The coaching engine of the fitness tracking system 100 uses the output of the fatigue identification engine to determine coaching to be provided to the user either during or after the workout. FIG. 9 shows a flowchart 900 of a method of coaching based on fatigue type. As described in further detail below, the method results in two different types of coaching provided to the user based on the detected type of fatigue (e.g., detection of a fatigue moment or detection of a certain fatigue level). The coaching provided to the user is primarily recommended actions for a current workout (or for future workouts), but may also include workout analysis and support for the user.

As shown in FIG. 9, the method 900 of coaching based on fatigue type during a workout begins at block 910 when workout data 226 is received from the sensor device 200 and/or the personal electronic device 300 of the fitness tracking system 100. As discussed previously herein, the workout data 226 includes a stream of workout data for a workout being performed by the user. The stream of workout data may include any of various foot action parameters such as speed, cadence, GCT, FSA, etc. The workout data may also include other data including heart rate, temperature, or other physiological data, or other movement data, such as GPS data.

After receipt of the workout data 226, the method continues to block 920 where the workout data is used by the fatigue identification engine to determine fatigue levels and fatigue moments for the user at various times during the workout. For example, as described above, the fatigue identification engine may periodically analyze the workout data every five seconds, thirty seconds, sixty seconds, or over some other interval and determines a fatigue level for the user and/or whether the user is experiencing a fatigue moment during that time period.

After the fatigue identification engine analyzes the workout data for a particular period of time, the method 900 moves to decision block 930 and a determination is made whether a fatigue moment occurred during the most recent period of time analyzed by the system. If a fatigue moment occurred, the method moves to block 940 and coaching based on an experienced fatigue moment is provided to the user via the personal electronic device 300 of the user. The coaching provided to the user in this instance is feedback that is particularly targeted to the occurrence of a fatigue moment which may be associated with the user "hitting the wall" or otherwise experiencing a significant rate of change in one or more workout parameters. In this situation, the coaching engine alerts the user via haptic, audio or visual cues on the user's personal electronic device 300 that the user is experiencing fatigue. Following the cue, the coaching engine may provide an audio message or written text to the personal electronic device 300 with particular coaching instructions. For example, an audio message may be delivered via a user's earbuds stating the following:

"It looks like your running form has changed. This might be a subtle sign of fatigue. You might not feel it but your form has changed. Adjust your [cadence, stride length, GCT, and/or FSA] by [SPM, mm, milliseconds, and/or degrees] in order to maintain your form. A change in form may negatively impact the effort required to run this pace."

As another example, a text message may be delivered to a user's smartphone or smartwatch stating the following:

"Watch your pace. It looks like you are becoming fatigued. If you are in the middle of your run consider slowing down so you can complete the distance without being overly worn down."

With continued reference to FIG. 9, if there is no recent fatigue moment at decision block 930, the method 900 continues to decision block 950, and a determination is made whether the most recently determined fatigue level is in excess of some threshold level such that coaching should be provided. The threshold level may be one of a plurality of different threshold levels that result in coaching to the user, and is not necessarily dependent upon the user reaching some unproductive fatigue level. For example, if the user's current fatigue level indicates that the user has moved from a low fatigue region to a medium fatigue region, this may be an indicative of the user crossing a fatigue level threshold that calls for coaching. If this is the case, and the user's fatigue level is in excess of the coaching threshold the method moves to block 960, and coaching is provided to the user associated with the user's particular fatigue level. In this instance, the coaching engine may alert the user via haptic, audio or visual cues on the user's personal electronic device 300 that the user's fatigue level has started to increase. Following the cue, the coaching engine may provide an audio message or written text to the personal electronic device 300 with particular coaching instructions. For example, an audio message may be delivered via a user's earbuds stating the following:

"Your fatigue level is starting to rise. Consider slowing your pace to allow completion of your desired distance without becoming overly fatigued."

As another example, an icon, color, text, number, or some combination thereof may be delivered to a graphical user interface of the user's personal electronic device indicating the user's current fatigue level (e.g., yellow colored characters "F5" indicative of a medium level 5 fatigue for the user, or red colored characters "F9" indicative of a high level 9 fatigue for the user). Thus, it will be recognized that the threshold level of decision block 950 may be one of several thresholds, and different coaching and or interface changes may be provided to the user depending on whether the user has crossed one of the various thresholds.

In addition to providing coaching during a user workout, such as that illustrated above in association with the flowchart of FIG. 9, the coaching engine is further configured to provide coaching after a user workout. The post-workout coaching includes both inter-run coaching (i.e., recommendations and analysis over a plurality of runs) and intra-run coaching (i.e., recommendations and analysis for a single run). In both instances, the coaching engine analyzes fatigue levels and fatigue moments to identify discrete moments of fatigue and/or the gradual onset of fatigue. The coaching engine then provides analysis and recommendations based on the identified fatigue types, fatigue levels across the workout (or workouts) and number of fatigue moments across the workout (or workouts).

Figure 10:
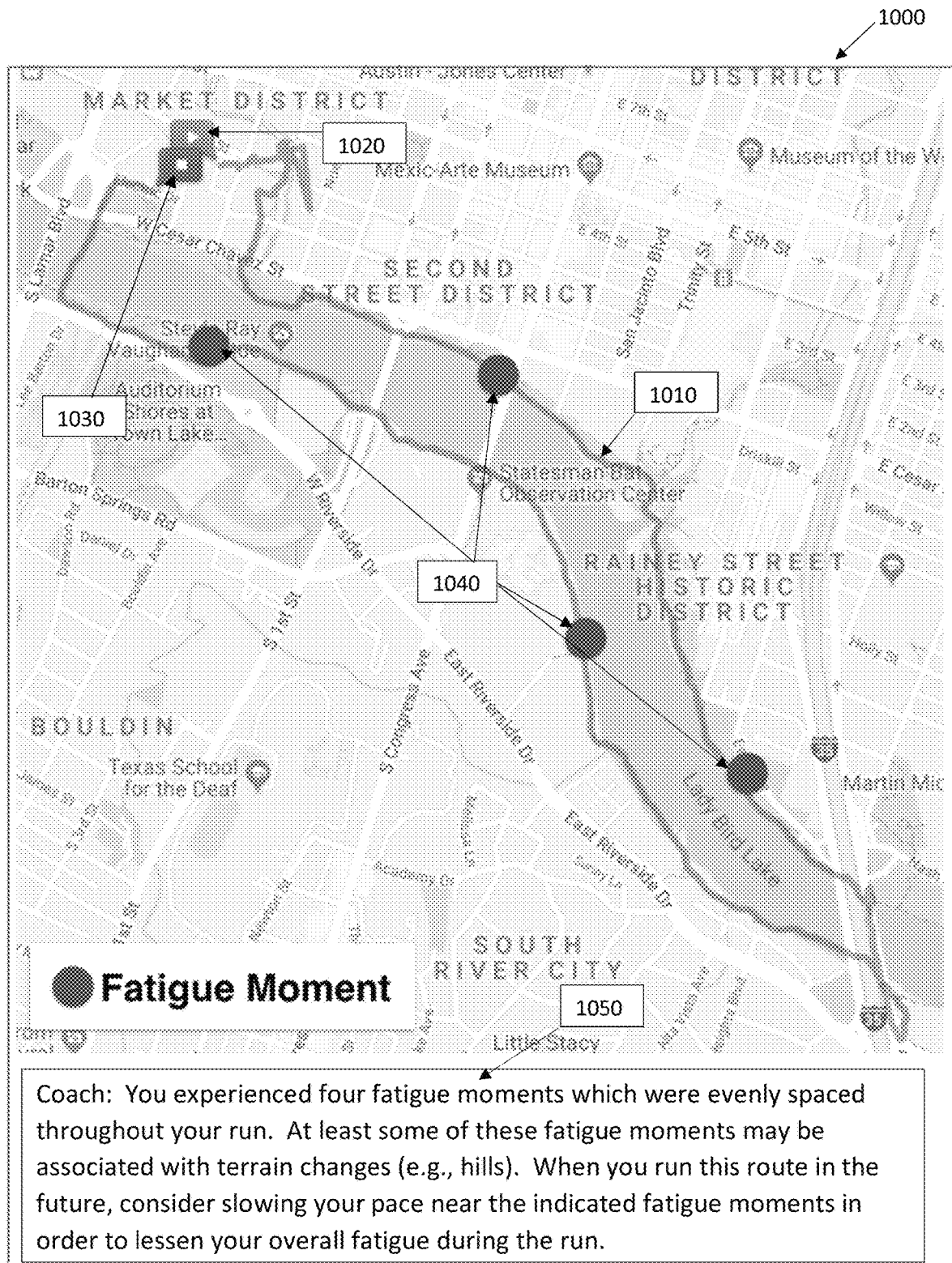
FIG. 10 is a graphical user interface showing coaching provided to a user after the user ran a route.

FIG. 10 shows an exemplary graphical user interface 1000 for a personal electronic device 300. The graphical user interface shows a map of a route 1010 recently completed by the user during a run, including the start position 1020 and end position 1030 of the user during the workout. A number of discrete fatigue moments 1040 are identified for the workout and flagged on the map. The coaching engine performs an analysis of the workout data and provides feedback to the user for the run. For example, the coaching engine may sum the number of fatigue moments (i.e., 4 moments of fatigue on this run), provide the lat/long coordinates of those discrete fatigue moments, and compare the fatigue moments for this run to those of past runs on the same route. Feedback may be provided to the user in a coaching box 1050 on the graphical user interface. As noted in the coaching box 1050, the provided coaching may be specific to runs for this particular route (e.g., "When you run this route in the future, consider . . . " or "The first fatigue moment appears to be associated with a climb; a fatigue moment at this point in the run is expected and a common occurrence; you recovered nicely.").

In addition to providing the coaching engine that provides recommended actions in association with various fatigue moments, the coaching engine may also provide coaching associated with various fatigue levels and/or the gradual onset of fatigue over time. Thus, it will be recognized that different coaching is provided to the user based on whether a detected type of fatigue is a fatigue moment or a particular fatigue level. For example, when the coaching engine receives an indication that a level of fatigue for the user has gradually increased over time and/or has crossed a fatigue threshold, the coaching engine may consider the coaching the user to avoid fatigue in the future (e.g., "You experienced the gradual onset of fatigue during this run which crossed into a high level prior to the final quarter of the run; consider running this route at a slower pace for future workouts.")

Figure 11:
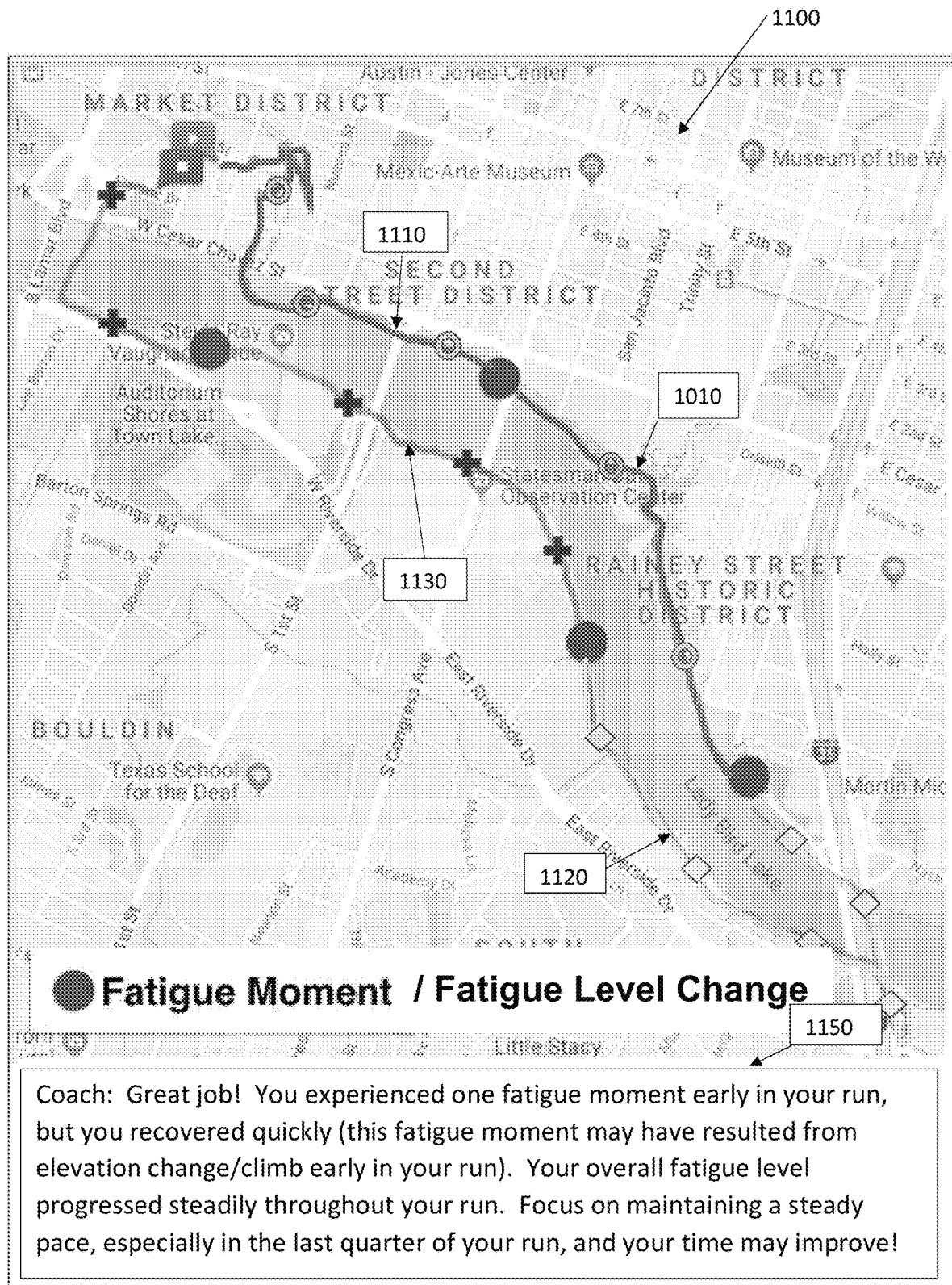
FIG. 11 shows an alternative embodiment of the graphical user interface of FIG. 10.

FIG. 11 shows a graphical user interface 1100 with the same route as that shown in FIG. 10. However, in FIG. 11, the graphical user interface includes a heat map overlaid on the route 1010 wherein different colors on the route represent different fatigue levels experienced by the user along the route. In the graphical user interface 1100, the first portion 1110 of the route includes circles representative of a first color indicative of a low fatigue level for the user (e.g., the first portion 1110 of the route is overlaid with a green color). The second portion 1120 of the route includes squares/diamonds representative of a second color indicative of a medium fatigue level for the user (e.g., the second portion 1120 of the route is overlaid with a yellow color). The third portion 1130 of the route is overlaid with a third color indicative of a high fatigue level for the user (e.g., the third portion 1130 of the route is overlaid with a red color). Fatigue moments 1140 are also indicated on the route. Accordingly, the graphical user interface 1100 of FIG. 11 is configured to quickly and intuitively summarize to the user different types of fatigue, and the extent of the fatigue, if appropriate. In particular, both "fatigue moments" 1140 and "fatigue levels" along various portions 1110, 1120, 1130 of the route are identified on the graphical user interface 1100. The values/extent of fatigue levels are presented to the user along with an indicated value for the fatigue levels (e.g., "low," "medium," and "high" levels associated with each of the colors green, yellow, and red). Furthermore, a coaching box 1150 is also provided for the workout. The coaching box 1150 provides encouragement (i.e., "Great Job!), analysis (" . . . you recovered quickly"), as well as recommended actions for future workouts (i.e., "Focus on maintaining a steady pace, especially in the last quarter of your run.").

As noted above, in the post workout experience, the coaching engine may deliver written or audio coaching. The coaching may include recommendation, analysis and insights based on how the athlete performed in association with the various fatigue types. Comparisons of fatigue between an identified workout and past workouts may also be made. The messages delivered by the coaching engine may be presented in any of various forms such as a paragraph of text, a bulleted list, or any of various other forms for communicating the coaching to the user. The analysis provided by the coaching engine will be dictated by a set of rules such as the following: fatigue moments, discrete fatigue levels and moments of transition, periods in which the athlete experienced fatigue moments (e.g., all fatigue moment during the first half of the run, all fatigue moments during the second half of the run, fatigue moments experienced evenly across the run), times in which the athlete started experiencing fatigue (e.g., during the first quarter of the run, during the last quarter of the run).

In addition to coaching for individual workouts, the coaching engine may also provide coaching across multiple workouts, thus providing an inter-workout experience. This inter-workout experience builds on the intra-workout experience, and is capable of using fatigue data across multiple workouts to provide coaching to the user for future workouts. For example, the fitness tracking system 100 may leverage discrete fatigue events or the onset of fatigue during multiple runs to coach the user on their overall training load. The coaching engine will look at the onset of fatigue (gradual or discrete) as well as various fatigue levels across these multiple runs. This information will be used to inform training load (i.e., how hard or how easy an athlete is training) and coach the user appropriately. As an example, if the majority of runs in a rolling window contain a significant number of fatigue events or fatigue onset, this could be a sign that the athlete is over training. Similarly, if the majority of runs in a rolling window contain no fatigue events, this could be a sign that the athlete could be training harder. When the coaching engine arrives at a determination of undertraining or overtraining, the analysis of undertraining or overtraining is delivered to the athlete along with recommendations for future workouts. Example recommendations associated with detected undertraining or overtraining include the following:

increase/decrease weekly mileage;
  increase/decrease the percentage of time run at a relative pace (e.g., the athletes predicted 5 k race pace);
  strength training exercises;
  foam rolling exercises;
  stretching exercises;
  increasing/decreasing the duration/distance of a single run;

In each instance of coaching, recommendations to the athlete are personalized based on the athlete's personal situation (e.g., over training will get different recommendations than under training). Furthermore, meta-information is used to inform the business rules or messaging logic associated with the inter-run fatigue coaching system. For example, meta information may include any of the following:

relative effort for a run (e.g., was it an "interval run");
  relative distance for a run (e.g., was it a "long run");
  terrain for a run, such as a "hilly" run (e.g., a run where the relative ascent exceeds some threshold);
  relative pace for the run (e.g., the run exceeded some minimum pace);
  the type of workout or activity to the extent that it affects the athlete's running form (e.g., stroller run, dog run, etc.)

The herein described applications (e.g., the fatigue identification engine, the coaching engine, and the associated user interfaces) improve the functioning of the fitness tracking system 100, the sensor device 200, the personal electronic device 300 and/or remote server 400, respectively or in combination by enabling it/there to provide robust collection of workout data, fatigue data, and associated coaching with minimal user effort to obtain such coaching (i.e., with a minimum amount of button presses or other user interactions). In particular, the fitness tracking system 100 is configured to obtain workout data and provide coaching that was not previously available to the user. The associated devices that are able to record workout data and provide fatigue identification and coaching allow the fitness tracking system to operate more effectively and efficiently for the user, thus allowing the user to more easily achieve their fitness goals, thus improving user retention of the fitness (racking system and real health outcomes for the users.

The foregoing detailed description of one or more exemplary embodiments of the fitness tracking system 100 has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

What is claimed is:

1. A method of operating a fitness tracking system comprising:
  receiving at least one first value for at least one user movement parameter from a sensor carried by a user during a first period of time during a workout;
  receiving at least one second value for the at least one user movement parameter from the sensor during the first period of time during the workout;
  determining a fatigue level of the user based at least in part on the received at least one first value and at least one second value;
  determining a rate of change for the at least one user movement parameter based on the first and second values received during the first period of time;
  determining whether the rate of change exceeds a threshold rate of change during the first period of time;
  identifying a fatigue moment associated with the first period of time when the rate of change exceeds the threshold rate of change;
  determining a first recommended action for the user in response to the fatigue moment;
  providing an indication of the fatigue moment and the first recommended action to the user in real time via a user interface during the workout;
  after identification of the fatigue moment during the first period of time, determining a fatigue level during a second period of time and whether another fatigue moment occurred during the second period of time;
  when another fatigue moment did not occur during the second period of time, determining whether the determined fatigue level exceeded a coaching threshold during the second period of time;
  determining a second recommended action for the user based on the fatigue level; and
  providing an indication of the fatigue level and the second recommended action to the user via the user interface during the workout.

2. The method of claim 1 wherein identifying a fatigue moment includes determining a workout time or a geographic location where the fatigue moment occurred.

3. The method of claim 2 wherein providing an indication of the fatigue moment includes providing an indication of the geographic location of the fatigue moment on a map associated with the user workout.

4. The method of claim 1 further including determining a workout time or a geographic location where the fatigue moment occurred and providing the indication of the geographic location of the fatigue moment on the user interface after the workout.

5. The method of claim 1 wherein providing the indication of the fatigue moment occurs during the user workout.

6. The method of claim 5 wherein the user interface is a graphical user interface, a haptic feedback device, or an acoustic device.

7. The method of claim 1 wherein the at least one user movement parameter includes one or more of foot ground contact time, foot strike angle, cadence, stride length and speed.

8. The method of claim 1 wherein the sensor is embedded in a sole of an article of footwear worn by the user.

9. The method of claim 1 wherein the at least one user movement parameter includes a plurality of parameters such that at least one first value includes a first set of values and the at least one second value includes a second set of values, and wherein determining the fatigue level includes performing a dimensionality reduction method on the first set of values and the second set of values in order to create at least one additional parameter indicative of fatigue status.

10. The method of claim 9 wherein the dimensionality reduction method is principal component analysis.

11. The method of claim 9 further comprising determining another recommended action for the user based on both (i) a first fatigue level and a first workout time associated therewith and (ii) a second fatigue level and a second workout time associated therewith.

12. The method of claim 1 wherein the first recommended action is based exclusively on a plurality of fatigue moments that occurred during the workout.

13. The method of claim 1 wherein the first recommended action is based on a plurality of fatigue moments including the fatigue moment that occurred during the workout and additional fatigue moments that occurred during additional workouts.

* * * * *